United States Patent
Kuhrts

(10) Patent No.: US 9,907,823 B1
(45) Date of Patent: Mar. 6, 2018

(54) WATER-SOLUBLE PHYTOCANNABINOID FORMULATIONS

(71) Applicant: Octarine Technologies LLC, Fairfield, CA (US)

(72) Inventor: Eric Kuhrts, Fairfield, CA (US)

(73) Assignee: Eric H. Kuhrts, Fairfield, CA (US)

( * ) Notice: Subject to any disclaimer, the term of this patent is extended or adjusted under 35 U.S.C. 154(b) by 0 days.

(21) Appl. No.: 14/791,181

(22) Filed: Jul. 2, 2015

Related U.S. Application Data

(60) Provisional application No. 62/077,153, filed on Nov. 7, 2014.

(51) Int. Cl.

| | |
|---|---|
| A61K 36/185 | (2006.01) |
| A61K 9/00 | (2006.01) |
| A23L 2/52 | (2006.01) |
| A61K 9/20 | (2006.01) |
| A61K 9/48 | (2006.01) |
| A61K 31/05 | (2006.01) |
| A61K 9/107 | (2006.01) |
| A23L 1/30 | (2006.01) |

(52) U.S. Cl.
CPC .......... *A61K 36/185* (2013.01); *A23L 1/3002* (2013.01); *A23L 2/52* (2013.01); *A61K 9/0014* (2013.01); *A61K 9/0053* (2013.01); *A61K 9/0095* (2013.01); *A61K 9/107* (2013.01); *A61K 9/2013* (2013.01); *A61K 9/4858* (2013.01); *A61K 31/05* (2013.01); *A23V 2002/00* (2013.01)

(58) Field of Classification Search
CPC .. A61K 36/185; A61K 9/0095; A61K 9/2013; A61K 9/0014; A61K 9/0053; A61K 9/4858; A61K 31/05; A61K 9/107; A23L 2/52; A23V 2002/00
See application file for complete search history.

(56) References Cited

U.S. PATENT DOCUMENTS

| | | |
|---|---|---|
| 6,689,388 B2 | 2/2004 | Kuhrts |
| 6,953,593 B2 | 10/2005 | Kuhrts |
| 8,071,136 B2 | 12/2011 | Kuhrts |
| 8,349,375 B2 | 1/2013 | Kuhrts |
| 8,883,225 B2 | 11/2014 | Kuhrts |
| 2003/0228369 A1 | 12/2003 | Kuhrts |
| 2006/0068021 A1 | 3/2006 | Kuhrts |
| 2011/0054029 A1 | 3/2011 | Kuhrts |
| 2011/0281957 A1 | 11/2011 | Kuhrts |
| 2012/0059052 A1 | 3/2012 | Kuhrts |
| 2013/0123368 A1 | 5/2013 | Kuhrts |
| 2013/0245118 A1 | 9/2013 | Kuhrts |
| 2013/0287923 A1 | 10/2013 | Kuhrts |
| 2014/0235715 A1 | 8/2014 | Kuhrts |
| 2015/0182625 A1 | 7/2015 | Kuhrts |
| 2015/0209307 A1 | 7/2015 | Kuhrts |
| 2015/0224074 A1 | 8/2015 | Kuhrts |
| 2015/0290266 A1 | 10/2015 | Kuhrts |

*Primary Examiner* — Trevor Love
(74) *Attorney, Agent, or Firm* — Thorpe North & Western LLP

(57) ABSTRACT

Methods and formulations for increasing the water solubility and/or bioavailability of a phytocannabinoid compound is disclosed herein. In one example, a water-soluble phytocannabinoid formulation can comprise a phytocannabinoid; a non-ionic surfactant; and optionally, water. The weight ratio of phytocannabinoid content to non-ionic surfactant can be from 1:10,000 to 1:5.

43 Claims, 2 Drawing Sheets

WATER-SOLUBLE PHYTOCANNABINOID FORMULATIONS

The present application claims the benefit of U.S. Provisional Patent Application No. 62/077,153, which was filed on Nov. 7, 2014, the entirety of which is incorporated herein by reference.

BACKGROUND

Hemp is an industrial plant that can be grown on a large scale in many regions of the world. Hemp, also known as *cannabis*, has a long history of use in humans as an anticonvulsant, sedative, hypnotic, anti-depressant, analgesic, anti-inflammatory, anti-emetic, anti-spasmodic, and appetite-stimulator. *Cannabis* contains a broad spectrum of chemical compounds including: phytocannabinoids, terpenoids (essential oils), flavonoids, enzymes, and steroids. While delta-9-tetrahydrocannabinol (delta-9-THC) is believed to be the principle psychoactive component of hemp, other phytocannabinoids (such as cannabidiol, cannabinol, and cannabichromene) are thought to possess numerous medicinal properties without the psychoactive effects of delta-9-THC. However, the oral bioavailability of these phytocannabinoids is limited. For example, the oral bioavailability of cannabidiol was found to be about 6%. The limited bioavailability of these phytocannabinoids is believed to be because cannabidiol is a natural fat soluble compound that is hydrophobic and thus insoluble in water. Due to the many desirable properties of phytocannabinoids, such as cannabidiol, it would be advantageous to provide improved, stable, water soluble formulations, with enhanced bioavailability for human consumption in various convenient formulations such as juices, soft drinks, bottled water, and liquid concentrates.

BRIEF DESCRIPTION OF THE DRAWINGS

Features and advantages of the technology disclosed herein will be apparent from the detailed description that follows, taken in conjunction with the accompanying figures that together illustrate features of the technology. It is understood that these figures merely depict exemplary embodiments and are not, therefore, to be considered limiting in scope. Furthermore, it will be readily appreciated that the components, as generally described and illustrated in the figures herein, could be arranged and designed in a wide variety of different configurations.

Figure 1:
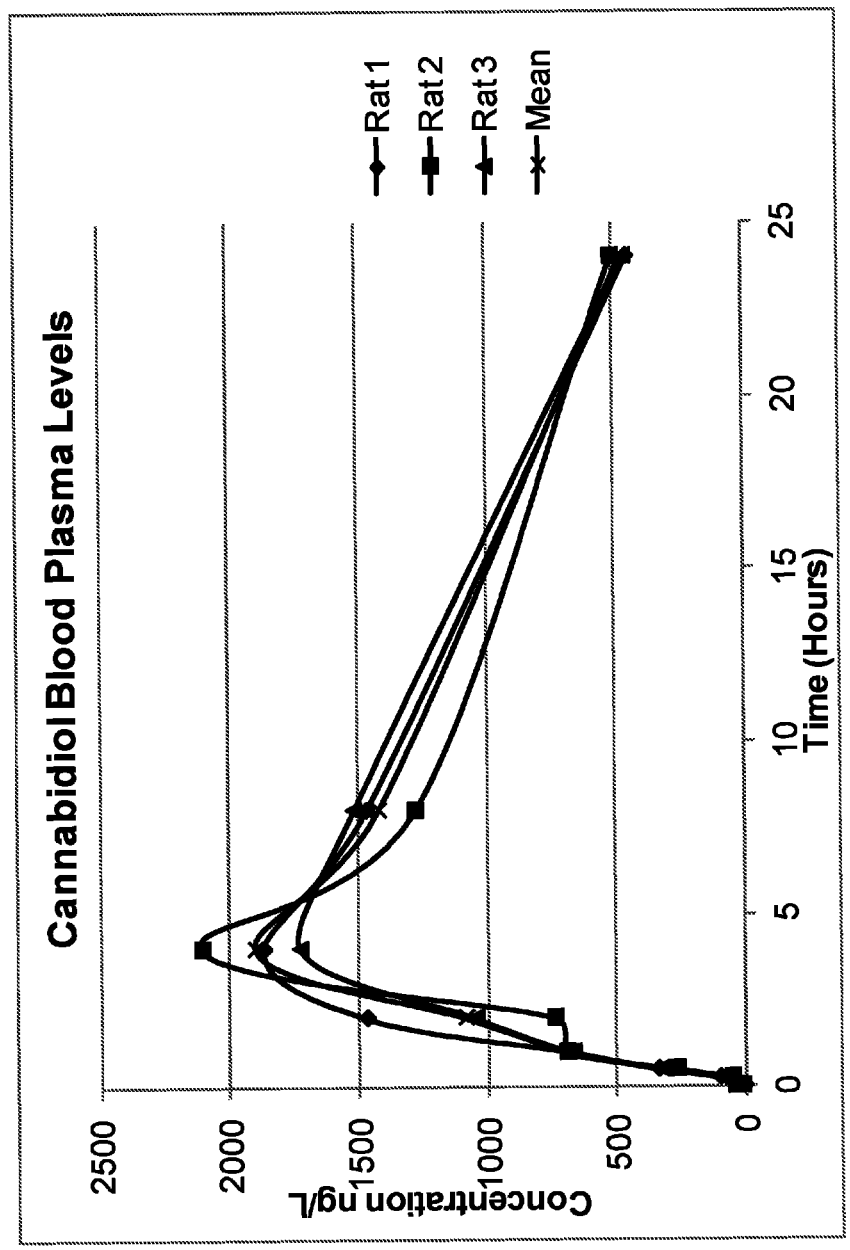
FIG. 1 shows the blood plasma levels of three rats administered a sample formulation of the water soluble cannabidiol oil as disclosed herein over a 24 hour period.

These figures are provided to illustrate various aspects of the technology and are not intended to be limiting in terms of results or components unless otherwise limited by the claims.

DETAILED DESCRIPTION

Reference will now be made to the exemplary embodiments and specific language will be used herein to describe the same. It will nevertheless be understood that no limitation of the scope of the invention is thereby intended. Alterations and further modifications of the inventive features illustrated herein, and additional applications of the principles of the disclosure as illustrated herein, which would occur to one skilled in the relevant art and having possession of this disclosure, are to be considered within the scope of the disclosure. It is also to be understood that this disclosure is not limited to the particular configurations, process steps and materials disclosed herein, as these may vary to some degree. Further, it is to be understood that the terminology used herein is used for the purpose of describing particular embodiments only, and is not intended to be limiting as the scope of the present disclosure.

The singular forms "a," "an," and "the" include plural referents unless the context clearly dictates otherwise. Thus, for example, reference to "a non-ionic surfactant" includes reference to one or more of such non-ionic surfactants.

The formulations described herein can be used in the context of "combination therapy" or "adjunct therapy" with other drugs to treat or otherwise provide a benefit with respect to a disease or other malady. This combination therapy can be sequential therapy where the patient is treated first with one drug and then the other or the two drugs are given simultaneously. The present disclosure includes combination therapy or adjunct therapy using the water soluble formulations of the present disclosure.

As used herein, the term "clear" is intended to relate to a solution or aqueous solution containing the natural lipophilic compound in a water containing solution (e.g. a beverage) that is free of visible particles of undissolved compound. A clear solution or clear aqueous solution includes both solutions as well as very fine dispersions that remain clear upon sitting undisturbed for one hour or more. Essentially no visible (to the naked eye) particles or micelles are present. When the clear aqueous solution is a beverage, the clear aqueous solution may sometimes not need to be shaken prior to consuming.

A "non-alcoholic" formulation, as used herein, is a formulation that does not include or includes only de minimis or trace amounts of methanol, ethanol, propanol or butanol.

The term "non-aprotic solvated," as used herein, means that water soluble aprotic solvents are absent or are included only in de minimis or trace amounts.

"Nutraceutical" includes lipophilic compounds or essential oils derived from natural sources such as *cannabis*, blueberries, grapes, other berries, soybeans, cocoa beans, tomatoes, green tea, turmeric, citrus fruit, other botanical sources, compounds produced synthetically as high purity compounds of an identical chemical structure to a naturally derived source, or produced through fermentation. Exemplary lipophilic natural compounds commonly used in nutraceuticals include the phytocannabinoids such as cannabidiol, terpenoids, essential oils such as β-caryophyllene, caryophyllene, pinene, linalool, limonene, phytol, nerolidol, myrcene, fatty acids such as linoleic, lenolenic, palmitic, stearidonic, stearic, oleic acid, arachidonoylethanolamide (anandamide), compounds such as co-enzyme Q-10, pterostilbene, lutein, lycopene, other essential flavor oils such as citrus oil, grapefruit seed extract, green tea extract, EGCG, cocoa extract, epigallocatechin gallate, epigallocatechin, epicatechin, catechin, epicatechin gallate, quercetin, curcumin, turmeric, D-limonene, lemon oil, carotenoids, astaxanthin, or phosphatidylserine.

The term "pharmaceutically acceptable salts" or "salts" is meant to include salts of the active compounds described herein which are prepared with nontoxic or relatively nontoxic acids or bases, depending on the particular substituent moieties found on the compounds described herein. When formulations of the present disclosure contain relatively basic functionalities, acid addition salts can be obtained by contacting the neutral form of such compounds with a sufficient amount of the desired acid, either neat or in a suitable inert solvent. When formulations of the present disclosure contain relatively acidic functionalities, base addition salts can be obtained by contacting the neutral form of such compounds with a sufficient amount of the desired base, either neat or in a suitable inert solvent. Certain specific formulations of the present disclosure contain both basic and acidic functionalities that allow the compounds to be converted with either base or acid addition salts. Examples of pharmaceutically acceptable base addition salts include sodium, potassium, calcium, ammonium, organic amino, magnesium salt, or similar salts thereof. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. The neutral forms of the compounds are typically regenerated by contacting the salt with a base or acid and isolating the parent compound in the conventional manner. The parent form of the compound can differ from the various salt forms in certain physical properties, such as, solubility in polar solvents.

As used herein, "phytocannabinoid" or "phytocannabinoid compound" means any of the following non-psychoactive compounds derived from *Cannabis*, and typically from the hemp plant. Exemplary phytocannabinoids include cannabidiol (CBD), cannabinol (CBN), cannabichromene (CBC), cannabichromenic acid (CBCA), cannabidiolic acid (CBDA), cannabidivarin (CBDV), cannabigerol (CBG), cannabigerolic acid (CBGA), or cannabigerivarin (CBGV). Cannabidiol (CBD) is one of the most abundant phytocannabinoids found in hemp.

"Phytocannabinoid oil" refers to oils that include phytocannabinoid compounds as well as other components that may also be present in the oil, such as small amounts of fatty acids such as oleic acid, palmitic acid, stearic acid, and octadecadienoic acid, etc., as well as essential oils. Depending on the extract, the phytocannabinoid content can be present at from less than 1 wt % (e.g., hemp oil) to up to 99 wt % or greater (highly purified extracts). In some examples, the phytocannabinoid oil can have from 20 wt % phytocannabinoid to 98 wt % phytocannabinoid compound(s). To illustrate, an 80 wt % extract oil can include 80 wt % CBD, for example.

As used herein, "prodrugs" are those compounds that readily undergo chemical changes under physiological conditions to provide the formulations of the present disclosure. Prodrugs can also be by chemical or biochemical methods in an ex vivo environment. For example, prodrugs can be slowly converted to the formulations of the present disclosure when placed in a transdermal patch reservoir with a suitable enzyme or chemical reagent.

As used herein, "subject" or "patient" is an organism that is treated using one of the methods of the present disclosure. In some embodiment, the subject is a mammalian subject, such as a human or a domestic animal.

A "water-solubilized" formulation, as used herein, includes the natural lipophilic compound, esters, metabolites, prodrugs, or salt thereof, a non-ionic surfactant, other compositional components, and water (e.g. a water containing liquid), but often does not include organic solvents (e.g. ethanol). In some embodiments, the water solubilized formulation is a transparent water soluble formulation.

As used herein, a plurality of items, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Removal of single components from a list or combining multiple lists together are considered to be fully supported herein as if each component were listed separately.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. This same principle applies to ranges reciting only one numerical value. Furthermore, such an interpretation should apply regardless of the breadth of the range or the characteristics being described.

With this in mind, many natural compounds (nutraceuticals) have been found to be potential therapeutic agents. Exemplary nutraceuticals include: the flavonoids or flavanols from green tea and cocoa (or dark chocolate) such as epigallocatechin gallate, epigallocatechin, epicatechin, catechin, and epicatechin gallate; flavonoids from grape-type fruits or berries such as resveratrol (3, 5, 4'-trihydroxystilbene); and pterostilbene derived from natural sources such as blueberries, grapes, other berries, or other botanical sources. Other natural compounds found to be beneficial for health include lutein (extracted from marigold flowers), lycopene (extracted from tomatoes), curcumin (1,7-Bis(4-hydroxy-3-methoxyphenyl)-1,6-heptadiene-3,5-dione, 99% by HPLC), turmeric, co-enzyme Q-10 (ubidecarenone, ubiquinone, ubiquinol), epigallocatechin gallate (EGCG) (derived from green tea), (–)-epicatechin (derived from cocoa powder), essential oils (such as citrus essential oils, grapefruit seed extracts, and D-limonene), carotenoids, astaxanthin, and phosphatidylserine.

Many flavonoids are lipophilic or fat soluble and exhibit very low solubility in water (hydrophobic). Some flavonoids can be virtually insoluble in water, and animal pharmacokinetic studies of oral doses have demonstrated very low bioavailability. Human studies with green tea extracts standardized to the active catechins, have demonstrated very low absorption, usually less than 1 wt % of the oral dose in animal or human studies. In order for nutraceuticals or any therapeutic molecular substance to be absorbed through the gastrointestinal tract, enter the blood, and eventually reach the organs and cells inside the body, the molecules should be finely dispersible or dissolvable in the aqueous phase of the intestinal fluid. Without dissolution, the substance will typically pass through the GI-tract and will not be absorbed at desirable concentrations.

As mentioned, one type of nutraceutical includes the phytocannabinoids derived from hemp such as cannabidiol. Phytocannabinoids are lipophilic compounds that are capable of being used therapeutically. Despite this, these compounds tend to be insoluble in water, often float on top of water, and will not form a stable water soluble solution that is crystal clear and remains that way over time. Hemp also contains various other essential oils or terpenes, and fatty acids that are lipophilic and insoluble in water. Some mixtures of certain fatty acids such as oleic acid have beneficial effects on other fatty acids contained in the diet by stimulating oxidation of those fatty acids. Exemplary potential nutraceutical components that can be derived from hemp are included in Tables A and B below.

TABLE A

Hemp Oil Fatty Acids

| Common Name | Scientific Name | Molecular Weight | CAS Number |
|---|---|---|---|
| Palmitic acid | Hexadecanoic acid | 256.42 | 57-10-3 |
| Stearic acid | Octadecanoic acid | 284.48 | 57-11-4 |
| Oleic acid | 9c-octadecenoic acid | 282.46 | 112-80-1 |
| Linoleic acid | 9c, 12c-octadecadienoic acid | 280.45 | 60-33-3 |
| Y-linoleic acid (GLA) | 6c, 9c, 12c-octadecatrienoic acid | 278.43 | 506-26-3 |
| α-linolenic acid (ALA) | 9c, 12c, 15c-octadecarienoic acid | 278.433 | 463-40-1 |
| Stearidonic acid | 6c, 9c, 12c, 15c-octadecatetraenoic acid | 276.417 | 20290-75-9 |

TABLE B

Hemp Oil Fatty Acid Profile (major fatty acids)

| Common Name | Scientific Name | Wt % |
|---|---|---|
| Palmitic acid (C16:0) | Hexadecanoic acid | 5-9 |
| Stearic acid (C18:0) | Octadecanoic acid | 2-3 |
| Oleic acid (C18:1) | 9c-octadecencoic acid | 8-16 |
| Linoleic acid (C18-2) | 9c, 12c-octadecadienoic acid | 50-70 |
| Y-linolenic acid (GLA) (18:3) | 6c, 9c, 12c-octadecatrienoic acid | 1-6 |
| α-linolenic acid (ALA) (C18:3) | 9c, 12c, 15c-octadecarienoic acid | 15-30 |
| Arachidic acid (C20:0) | Icosanoic acid | 0-2 |
| Stearidonic acid (SDA) | 6c, 9c, 12c, 15c-octadecatetraenoic acid | 0.5-1.5 |
| Palmitoleic acid (C16:1) | 9Z-hexadec-9-enoic acid | 0-0.5 |

The principle fatty acids (present in amounts greater than 1 wt %) found in hemp are linoleic, linolenic, oleic, palmitic, and stearic acids.

With this in mind, the present disclosure provides water-soluble phytocannabinoid formulations including a phytocannabinoid or a combination thereof and a non-ionic surfactant. For example, a water-soluble phytocannabinoid emulsion formulation can include a phytocannabinoid oil and a non-ionic surfactant, wherein the weight ratio of phytocannabinoid content to non-ionic surfactant is from 1:10,000 to 1:5. In another example, the formulation can be dissolved or finely dispersed in water.

In another example, a water-soluble phytocannabinoid emulsion formulation can include a phytocannabinoid oil containing a phytocannabinoid selected from the group consisting of cannabidiol (CBD), cannabinol (CBN), cannabichromene (CBC), cannabichromenic acid (CBCA), cannabidiolic acid (CBDA), cannabidivarin (CBDV), cannabigerol (CBG), cannabigerolic acid (CBGA), cannabigerivarin (CBGV), esters thereof, metabolites thereof, and mixtures thereof; and a non-ionic surfactant. The phytocannabinoid content and the non-ionic surfactant can be present in the formulation at a weight ratio from about 1:1,000 to about 1:5.

These formulations can also include mixtures of fatty acids and/or essential oils found in hemp. In some embodiments, the fatty acids can be present in amounts that are not naturally present in hemp oil. In other embodiments, the formulation can further comprise essential oils (terpenes), other fatty acids, esters thereof, salts thereof, metabolites thereof, prodrugs thereof, and mixtures thereof.

The phytocannabinoid compound can be selected from cannabidiol (CBD), cannabinol (CBN), cannabichromene (CBC), cannabichromenic acid (CBCA), cannabidiolic acid (CBDA), cannabidivarin (CBDV), cannabigerol (CBG), cannabigerolic acid (CBGA), and/or cannabigerivarin (CBGV). In one embodiment, the phytocannabinoid compound is cannabidiol. In another embodiment, the formulation can include a phytocannabinoid compound and certain amounts of fatty acids such as oleic acid, palmitic acid, stearic acid, and octadecadioic acid, as well as essential oils.

In some other embodiments, the water-soluble formulations containing phytocannabinoid compounds and/or fatty acids can be formulated for use in beverages or liquid concentrates.

The non-ionic surfactant can be a surface active agent that tends to be non-ionized in neutral solutions. Useful non-ionic surfactants can comprise non-ionic water soluble mono-, di-, and tri-glycerides; non-ionic water soluble mono- and di-fatty acid esters of polyethyelene glycol; non-ionic water soluble sorbitan fatty acid esters (e.g. sorbitan monooleates such as SPAN 80 and TWEEN 20 (polyoxyethylene 20 sorbitan monooleate)); polyglycolyzed glycerides; non-ionic water soluble triblock copolymers (e.g. poly(ethyleneoxide)/poly-(propyleneoxide)/poly(ethyleneoxide) triblock copolymers such as POLOXAMER 406 (PLURONIC F-127), and derivatives thereof. Examples of non-ionic water soluble mono-, di-, and tri-glycerides can include propylene glycol dicarpylate/dicaprate (e.g. MIGLYOL 840), medium chain mono- and diglycerides (e.g. CAPMUL and IMWITOR 72), medium-chain triglycerides (e.g. caprylic and capric triglycerides such as LAVRAFAC, MIGLYOL 810 or 812, CRODAMOL GTCC-PN, and SOFTISON 378), long chain monoglycerides (e.g. glyceryl monooleates such as PECEOL, and glyceryl monolinoleates such as MAISINE), polyoxyl castor oil (e.g. macrogolglycerol ricinoleate, macrogol glycerol hydroxystearate, macrogol cetostearyl ether), and derivatives thereof. Non-ionic water soluble mono- and di-fatty acid esters of polyethyelene glycol can include d-α-tocopheryl polyethyleneglycol 1,000 succinate (TPGS), poyethyleneglycol 660 12-hydroxystearate (SOLUTOL HS 15), polyoxyl oleate and stearate (e.g. PEG 400 monostearate and PEG 1750 monostearate), and derivatives thereof. Polyglycolyzed glycerides can include polyoxyethylated oleic glycerides, polyoxyethylated linoleic glycerides, polyoxyethylated caprylic/capric glycerides, and derivatives thereof. Specific examples include LABRAFIL M-1944CS, LABRAFIL M-2125CS, LABRA- SOL, SOFTIGEN, and GELUCIRE. In some embodiments, the non-ionic surfactant is a polyoxyl castor oil, or a derivative thereof.

In some embodiments, the water soluble formulations can comprise the phytocannabinoid compound, metabolite, ester, prodrug, or salt thereof, and various fatty acids in an emulsion. The phytocannabinoid emulsion can be combined with water to form a transparent water soluble formulation. A "transparent water soluble formulation," as disclosed herein, refers to a formulation that can be seen through with the naked eye and is optionally colored. In some embodiments, the transparent water soluble formulation does not contain particles (e.g. particles of undissolved lipophilic compound) visible to the naked eye. In some embodiments, the water soluble formulation does not include visible macro-micelles (micelles visible to the naked eye) in water. In certain embodiments, light may be transmitted through the transparent water soluble formulations without diffusion or scattering. Thus, in some embodiments the transparent water soluble formulations are not opaque, cloudy, or milky-white. Transparent water soluble formulations as disclosed herein do not include milky-white emulsions or suspensions in vegetable oil such as corn oil. Transparent water soluble formulations are also typically not formed by first dissolving the compound in alcohol, and then mixed with water. Thus, in some embodiments, the water soluble formulation can comprise a non-alcoholic formulation.

In yet another embodiment, the formulation can comprise a non-aprotic solvated formulation. Water soluble aprotic solvents are water soluble non-surfactant solvents in which the hydrogen atoms are not bonded to an oxygen or nitrogen and therefore cannot donate a hydrogen bond.

In still other embodiments, the water soluble formulation does not include (or includes only de minimis or trace amounts) a non-polar aprotic solvent. Non-polar aprotic solvents are aprotic solvents whose molecules exhibit a molecular dipole of zero or approximately zero. Exemplary non-polar aprotic solvents can include hydrocarbons, such as alkanes, alkenes, and alkynes.

In further embodiments, the water soluble formulation does not include (or includes only de minimis or trace amounts) a polar aprotic solvent. Polar aprotic solvents are aprotic solvents whose molecules exhibit a molecular dipole moment but whose hydrogen atoms are not bonded to an oxygen or nitrogen atom. Examples of polar aprotic solvents include aldehydes, ketones, dimethyl sulfoxide (DMSO), and dimethyl formamide (DMF). In other embodiments, the water soluble formulation does not include (or includes only de minimis or trace amounts) of dimethyl sulfoxide. Thus, in some embodiments, the water soluble formulation does not include DMSO. In another embodiment, the water soluble formulation does not include DMSO or ethanol.

The water soluble formulation of the present disclosure can comprise formulations dissolved in water (i.e. aqueous formulations), as well as formulations without water, that are suitable for use in soft-gelatin capsules, that form soluble solutions in gastric fluid after ingestion. In most embodiments, the water soluble formulations form a transparent water soluble formulation when added to water.

In some embodiments, the water soluble formulation consists essentially of the phytocannabinoid compound (e.g., the lipophilic natural compound per se or the ester, metabolite, prodrug, and/or salt thereof), and a non-ionic surfactant. In one embodiment, the phytocannabinoid compound is cannabidiol. Where a water soluble formulation "consists essentially of" the lipophilic natural compound and a non-ionic surfactant, the formulation includes the lipophilic natural compound and the non-ionic surfactant, and optionally additional components widely known in the art to be useful in nutraceutical formulations, such as preservatives, excipients, pH modifiers, taste enhancers, buffers, water, etc. As a specific example, a water soluble formulation that "consists essentially of" the phytocannabinoid compound, ester, or salt thereof does not include any significant formulation additive or component that would materially affect the basic and novel properties of the invention.

In other embodiments, a free form of the compound can prepared due to a higher concentration of the active compound. Certain formulations of the present disclosure can exist in unsolvated forms as well as solvated forms, including hydrated forms. In general, the solvated forms are equivalent to unsolvated forms and are encompassed within the scope of the present disclosure. Certain formulations of the present disclosure may exist in multiple crystalline or amorphous forms. In general, all physical forms are equivalent for the uses contemplated by the present disclosure and are intended to be within the scope of the present invention.

Certain formulations of the present disclosure possess asymmetric carbon atoms (optical centers) or double bonds, and the racemates, diastereomers, tautomers, geometric isomers and individual isomers are encompassed within the scope of the present disclosure.

The formulations of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the formulations of the present disclosure, whether radioactive or not, are encompassed within the scope of the present disclosure.

In addition to salt forms, the present disclosure provides compounds, which are in a prodrug form, metabolites, esters, or the like.

In some embodiments, the phytocannabinoid compound is present in the water soluble emulsion formulation at a concentration of at least 0.1 wt %, 1%, 5%, 10%, 20%, 25%, 30%, 35%, 45%, 45%, or 50% by weight. In other embodiments, the compounds can be present in the water soluble emulsion formulation at a concentration from 0.01 to 80%, 0.1% to 80%, 1% to 80%, 5% to 50%, 10% to 35%, or 20% to 25% (by weight). In some embodiments, the phytocannabinoid compound is present in the water solubilized formulation (where water is added to the emulsion) at a concentration of at least 0.01 wt %, 0.1 wt %, 1%, 5%, 10%, 20%, 25%, 30%, 35%, 45%, 45%, or 50% by weight. In other embodiments, the compounds can be present in the water solubilized formulation (where the water is added) at a concentration from 0.001% to 50%, 0.01% to 50%, 0.1% to 50%, 1% to 40%, 5% to 35%, or 10% to 25% (by weight).

The compound may also be present (e.g. in a beverage formulation) at a concentration with added water from 0.5 mg to 250 mg per 3.3 fluid oz, or around 2 mg/ml to 10 mg/ml. In other embodiments, the compound is present at a concentration from 0.01 mg/ml to 50 mg/ml. The concentration range would be from 0.1% to 30% by weight for the surfactant, or 0.01 mg/ml to 50 mg/ml for the phytocannabinoid compound, with a more typical concentration around 10 mg/ml of actual phytocannabinoid, depending on the purity of the phytocannabinoid oil. This can be, for examples, at a ratio of the phytocannabinoid oil to surfactant of 1:1,000 to 1:5 by weight (about 0.1 wt % to about 20 wt % phytocannabinoid oil in the oil/surfactant emulsion). That being said, as the phytocannabanoid content in oil extracts can range from less than 1 wt % phytocannabinoid compound to essentially 100 wt % phytocannabanoid, the phytocannabanoid content to non-ionic surfactant weight ratio can be from 1:10,000 to 1:5, from 1:5,000 to 1:5, or from 1:1000 to 1:5. In another example, the phytocannabinoid compound may be present at about 0.1 mg/ml to 50 mg/ml, or around 20 mg/ml, or at least 1 mg/ml (in cases where water is present, or when water is not present). When water is not present, the phytocannabinoid compound may be present at from 0.1 mg/ml to 75 mg/ml in some examples.

In another aspect, the present disclosure provides a method for enhancing the bioavailability of the phytocannabinoid compounds in a subject. The method includes combining a phytocannabinoid oil (including metabolites or salt thereof) with a non-ionic surfactant to form a surfactant-lipophilic compound mixture. The surfactant-lipophilic compound mixture may be administered to the subject directly, or admixed with water and administered, thereby enhancing the bioavailability of the phytocannabinoid compound. The bioavailability is enhanced compared to the bioavailability of the compound in the absence of non-ionic surfactant.

In another aspect, the present disclosure provides a method of dissolving a phytocannabinoid (including a metabolite or salt thereof) in water. The method includes combining a phytocannabinoid oil with a phytocannainoid therein with a non-ionic surfactant that has been warmed to form a surfactant-phytocannabinoid mixture. Subject non-ionic surfactants may be assayed for their ability to solubilize the phytocannabinoid oil using any appropriate method. Typically, a heated, non-ionic surfactant can be contacted with the phytocannabinoid oil and mixed mechanically and/or automatically using a shaker or heated mixing vessel device. This can be done without other added ingredients, but in some examples, warm water may be optionally added. In one example, the water may be used where the compound and/or surfactant is in powder form. In one embodiment, the non-ionic surfactant can be warmed to a temperature of at least 90° F. In another embodiment, the non-ionic surfactant can be warmed to a temperature of at least 200° F. In these examples, the solution is heated to a temperature of at least 90° F., at least 120° F., at least 150° F., or at least 200° F. The heating temperature can be selected to avoid chemical breakdown of the lipophilic natural compound or lipophilic natural compound metabolite and non-ionic surfactant. This temperature is usually, but not limited, to within the range from about 90° F. to about 180° F. In one embodiment the temperature range is from about 100° F. to about 125° F.

In one embodiment, when the formulation is for inclusion in a soft-gelatin capsule, the warm phytocannabinoid compound and surfactant can be combined with other oils, such as oleic acid or olive oil, or without these oils, and filled into capsules without water. The heating temperature can be selected to avoid chemical breakdown of the phytocannabinoid compound and/or non-ionic surfactant. The temperature range is usually, but not limited, to a range from about 90° F. to about 180° F. In one embodiment the temperature range is from about 100° F. to about 125° F.

The surfactant-phytocannabinoid mixture can then be combined with water that has been warmed, thereby dissolving (or very finely dispersing) the compound in water. In one embodiment, the water can be warmed to a temperature of at least 90° F. In another embodiment, the water can be warmed to a temperature of at least 200° F. The temperature is usually, but not limited, to within the range from about 90° F. to about 180° F. In one embodiment, the temperature range is from about 100° F. to about 125° F. In some embodiments, the resulting solution is a water soluble formulation or transparent water soluble formulation as described above. For example, the resulting solution may be a water soluble formulation that can be a crystal clear solution, with no particles visible to the naked eye.

The resulting solution may be visually inspected for colloidal particles to determine the degree of solubility of the compound. Alternatively, the solution may be filtered and analyzed to determine the degree of solubility. For example, a spectrophotometer may be used to determine the concentration of the compound present in the filtered solution. Typically, the test solution is compared to a positive control containing a series of known quantities of pre-filtered lipophilic natural compound solutions to obtain a standard concentration versus UV/VIS absorbance curve. Alternatively, high performance liquid chromatography may be used to determine the amount of the compound in solution.

High throughput solubility assay methods are known in the art. Typically, these methods involve automated dispensing and mixing of solutions with varying amounts of non-ionic surfactants, lipophilic natural compound, and optionally other co-solvents. The resulting solutions may then be analyzed to determine the degree of solubility using any appropriate method. For example, the Millipore MultiScreen Solubility filter Plate® with modified track-etched polycarbonate, 0.4 µm membrane is a single-use, 96-well product assembly that includes a filter plate and a cover. This device is intended for processing aqueous solubility samples in the 100-300 µL volume range. The vacuum filtration design is compatible with standard, microtiter plate vacuum manifolds. The plate is also designed to fit with a standard, 96-well microtiter receiver plate for use in filtrate collection. The MultiScreen Solubility filter Plate® has been developed and QC tested for consistent filtration flow-time (using standard vacuum), low aqueous extractable compounds, high sample filtrate recovery, and its ability to incubate samples as required to perform solubility assays. The low-binding membrane has been specifically developed for high recovery of dissolved organic compounds in aqueous media.

The aqueous solubility assay allows for the determination of phytocannabinoid solubility by mixing, incubating, and filtering a solution in the MultiScreen Solubility filter plate. After the filtrate is transferred into a 96-well collection plate using vacuum filtration, it is analyzed by UV/VIS spectroscopy to determine solubility. Additionally, LC/MS or HPLC can be used to determine compound solubility, especially for compounds with low UV/VIS absorbance and/or compounds with lower purity. For quantification of aqueous solubility, a standard calibration curve may be determined and analyzed for each compound prior to determining aqueous solubility.

Test solutions may be prepared by adding an aliquot of concentrated drug or compound. The solutions are mixed in a covered 96-well MultiScreen Solubility filter plate for 1.5 hours at room temperature. The solutions are then vacuum filtered into a 96-well, polypropylene, V-bottomed collection plate to remove any insoluble precipitates. Upon complete filtration, 160 µL per well are transferred from the collection plate to a 96-well UV analysis plate and diluted with 40 µL per well of acetonitrile. The UV/VIS analysis plate is scanned from 260 nm to 500 nm with a UV/VIS microplate spectrometer to determine the absorbance profile of the test compound.

Thus, one skilled in the art may assay a wide variety of non-ionic surfactants to determine their ability to solubilize lipophilic natural compounds.

Also presented herein are pharmaceutical compositions. The pharmaceutical composition may include the phytocannibinoid, such as cannabidiol, an ester or metabolite of a phytocannabinoid, a non-ionic surfactant, and a pharmaceutically acceptable excipient.

The pharmaceutical composition can be in any appropriate dosage form can be used for administration of the water soluble formulation of the present disclosure, such as oral, parenteral, and topical dosage forms. Oral preparations include tablets, pills, powder, dragees, capsules (e.g. soft-gel capsules), liquids, lozenges, gels, syrups, slurries, beverages, suspensions, etc., suitable for ingestion by the patient. The formulations of the present disclosure can also be administered by injection, that is, intravenously, intramuscularly, intracutaneously, subcutaneously, intraduodenally, or intraperitoneally. The formulations can also be administered by inhalation, for example, intranasally. In other embodiments, the formulations of the present disclosure can be administered transdermally by a topical route, formulated as applicator sticks, solutions, suspensions, emulsions, gels, creams, ointments, pastes, jellies, paints, powders, and aerosols. A water soluble formulation as described herein may be sprayed directly onto the skin. In yet another embodiment, the formulations can be administered by in intraocular, intravaginal, and intrarectal routes including suppositories, insufflation, powders and aerosol formulations. In further embodiments the formulations can be adapted for oral administration. The formulations can also be delivered as microspheres for slow release in the body. For example, microspheres can be administered via intradermal injection of drug-containing microspheres, which slowly release subcutaneously, or, as microspheres for oral administration. Both transdermal and intradermal routes can afford constant delivery for weeks or months.

Pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration of solid form pharmaceuticals are well described in the scientific and patent literature.

Suitable carriers can include magnesium carbonate, magnesium stearate, talc, sugar, lactose, pectin, dextrin, starch (from corn, wheat, rice, potato, or other plants), gelatin, tragacanth, a low melting wax, cocoa butter, sucrose, mannitol, sorbitol, cellulose (such as methyl cellulose, hydroxypropylmethyl-cellulose, or sodium carboxymethylcellulose), and gums (including arabic and tragacanth), as well as proteins such as gelatin and collagen. If desired, disintegrating or co-solubilizing agents may be added, such as the cross-linked polyvinyl pyrrolidone, agar, alginic acid, or a salt thereof, such as sodium alginate. In powders, the carrier can be a finely divided solid, which is in a mixture with the finely divided active component. In tablets, the active component can be mixed with the carrier having the necessary binding properties in suitable proportions and compacted in the shape and size desired.

Dragee cores can be provided with suitable coatings such as concentrated sugar solutions, which can also contain gum arabic, talc, polyvinylpyrrolidone, carbopol gel, polyethylene glycol, titanium dioxide, lacquer solutions, suitable organic solvents or solvent mixtures, and combinations thereof. Dyes or pigments may be added to the tablets or dragee coatings for product identification or to characterize the quantity of active compound (i.e., dosage). Pharmaceutical preparations of the present disclosure can also be used orally using, for example, push-fit capsules made of gelatin, as well as soft, sealed capsules made of gelatin and a coating such as glycerol or sorbitol. Push-fit capsules can contain the lipophilic natural compound mixed with a filler or binders such as lactose or starches, lubricants such as talc or magnesium stearate, and optionally stabilizers. In soft capsules, the compound may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby allowed to solidify.

Liquid form preparations include solutions, suspensions, beverages, and emulsions, for example, water or water/propylene glycol solutions. For parenteral injection, liquid preparations can be formulated in solution in an aqueous polyethylene glycol solution.

Aqueous solutions and beverages suitable for oral use can be prepared by dissolving the active component in water and optionally adding suitable colorants, flavors, stabilizers, and thickening agents. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents, and/or one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations can contain, in addition to the active component, colorants, flavors, stabilizers, buffers, artificial and natural sweeteners, dispersants, thickeners, solubilizing agents, and the like.

Emulsions can be formulated by combining the phytocannabinoid compound with a specific mixture of fatty acids, such as oleic, stearic, palmitic, trans-octadecadienoic acid, and arachidic acids. The emulsions can contain other essential oils contained in the hemp plant such as the terpenes myrcene, limonene, alpha & beta-pinene, linalool, b-caryophyllene, caryophyllene oxide, humulene, nerolidol, and phytol. The emulsions can contain a thickening agent, such as beeswax, hard paraffin or cetyl alcohol. Sweetening agents can be added to provide a palatable oral preparation, such as glycerol, sorbitol, or sucrose. These formulations can be preserved by the addition of an antioxidant such as ascorbic acid. The formulations can also be in the form of oil-in-water emulsions. The oily phase can be a vegetable oil or a mineral oil, described above, or a mixture of these. Suitable emulsifying agents include: naturally-occurring gums, such as gum acacia and gum tragacanth; naturally occurring phosphatides, such as soybean lecithin; esters or partial esters derived from fatty acids; and hexitol anhydrides, such as sorbitan mono-oleate; and condensation products of these partial esters with ethylene oxide, such as polyoxyethylene sorbitan mono-oleate. The emulsion can also contain sweetening agents and flavoring agents, as in the formulation of syrups and elixirs. Such formulations can further contain a demulcent, a preservative, or a coloring agent.

The formulations of the disclosure can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM to 50 mM histidine, 0.1 wt % to 2 wt % sucrose, and/or 2 wt % to 7 wt % mannitol at a pH range of 4.5 to 5.5 that is combined with buffer prior to use.

In another embodiment, the formulations of the present disclosure can be useful for parenteral administration, such as intravenous (IV) administration or administration into a body cavity or lumen of an organ. The formulations for administration will commonly comprise a solution of phytocannbinoid dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid and various terpenes can likewise be used in the preparation of injectables. These solutions are sterile and generally free of undesirable matter. These formulations may be sterilized by conventional, well known sterilization techniques. The formulations can contain pharmaceutically acceptable auxiliary substances to approximate physiological conditions such as pH adjusting and buffering agents, toxicity adjusting agents, e.g., sodium acetate, sodium chloride, potassium chloride, calcium chloride, sodium lactate, and the like. The concentration of lipophilic natural compound in these formulations can vary widely and can be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1, 3-butanediol.

In another embodiment, the formulations of the present disclosure can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the lipophilic natural compound, metabolite, or ester thereof into the target cells in vivo.

The formulations can be administered as a unit dosage form. In such form the preparation can be subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation can be varied or adjusted according to the particular application and the potency of the active component. The composition can, if desired, contain other compatible therapeutic agents.

The amount of phytocannabinoid compound adequate to treat a disease (e.g. through modulation of VEGF, COX, cell proliferation), is defined as a "therapeutically effective" dose. The dosage schedule and amounts effective for this use, i.e., the "dosing regimen," will depend upon a variety of factors, including the stage of the disease or condition, the severity of the disease or condition, the general state of the patient's health, the patient's physical status, age, and the like. In calculating the dosage regimen for a patient, the mode of administration also is taken into consideration. An effective amount of the water soluble formulation of the present disclosure is an amount sufficient to achieve the intended purpose of a method of the present invention, such as treating a particular disease state in a subject (e.g. a human subject). One skilled in the art is capable of determining the appropriate dosage.

The dosage regimen also takes into consideration pharmacokinetics parameters well known in the art, i.e., the rate of absorption, bioavailability, metabolism, clearance, and the like (for example, the latest Remington's, supra). The state of the art allows the clinician to determine the dosage regimen for each individual patient and disease or condition treated.

Single or multiple administrations of phytocannabinoid formulations can be administered depending on the dosage and frequency tolerated by the patient. The formulations should provide a sufficient quantity of active agent to effectively treat the disease state. Lower dosages can be used when the drug is administered to an anatomically secluded site in contrast to when administration is orally, into the blood stream, into a body cavity, or into a lumen of an organ. Substantially higher dosages can be used in topical administration. Actual methods for preparing parenterally administrable lipophilic natural compound formulations are known or apparent to those skilled in the art.

In other embodiments, at least 0.5 mg, 1 mg, 2 mg, 3 mg, 4 mg, 5 mg, 10 mg, 20 mg, 30 mg, 40 mg, 50 mg, 100 mg, 200 mg, 300 mg, 400 mg, 500 mg, or 1 g of the compound is present in the water soluble beverage formulation. In other embodiments, 0.1 mg to 2 g, 0.5 mg to 1 g, 1 mg to 500 mg, 1 mg to 100 mg, 1 mg to 50 mg, 1 mg to 10 mg, or 1 mg to 5 mg of lipophilic natural compound is present in the water soluble beverage formulation.

After a pharmaceutical composition including the lipophilic natural compound of the present disclosure has been formulated in an acceptable carrier, it can be placed in an appropriate container and labeled for treatment of an indicated condition. For administration of the compound, such labeling can include, e.g., instructions concerning the amount, frequency, and method of administration.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the present disclosure may be combined with any one or more other features of any other embodiment of the present disclosure, without departing from the scope of the invention. For example, the features of the formulations are equally applicable to the methods of treating disease states described herein.

EXAMPLES

The following examples below are meant to illustrate certain embodiments of the present disclosure, and are not intended to limit the scope of the invention, but instead to provide further detail in connection with what are presently deemed to be the most practical and preferred embodiments of the present disclosure.

Example 1

Water soluble compositions of the phytocannabinoid cannabidiol (CBD) were formulated by admixing cannabidiol oil with the non-ionic surfactant macrogolglycerol hydroxystearate (polyoxyl 40 castor oil) at about 1:10 weight ratio of oil to surfactant. The cannabidiol oil contained 80 wt % cannabidiol (CBD). The polyoxyl castor oil (non-ionic surfactant) was heated and stirred to a temperature of about 120° F. Then the cannabidiol oil was added slowly and mixed until a clear viscous emulsion phase formulation with dissolved CBD oil was formed (cannabidiol emulsion). Water was boiled at 212° F. The heated water was then slowly added to the cannabidiol emulsion until a crystal clear solution was formed. During the emulsion phase, the mixture took on a dark purple color. This color was also evident after the aqueous phase when the water became a part of the formulation. The only difference was that the purple was a lighter color. This color change was unexpected, and the net result is a visually desirable color that is much more appealing to the consumer.

The weight percentage of each component in the water soluble composition is presented in Table 1.

TABLE 1

Water Soluble Cannabidiol Composition
Water Soluble CBD Formula

| Ingredients | Wt % |
| --- | --- |
| Cannabidiol Oil (80 wt % CBD) | 3 |
| Water | 66.7 |
| Macrogolglycerol hydroxystearate 40 | 30 |
| Sodium Benzoate | 0.06 |
| Potassium Sorbate | 0.04 |
| Citric Acid | 0.2 |
| Total | 100 |

The water soluble formulation above was analyzed by HPLC and found to contain 2.4 wt %, or 24 mg/ml cannabidiol. It is noted that in some embodiments, as shown in the table above, the formulation may also include pH modifiers, preservatives, etc., in minor amounts.

Example 2

1 ml of the formula prepared in accordance with Table 1 was further dissolved in 8 oz. of water to make an unsweetened, unflavored medicinal water. The resulting beverage was crystal clear and remained so indefinitely.

Example 3

Water soluble compositions of grapefruit seed extract were formulated containing macrogolglycerol hydroxystearate (polyoxyl 40 castor oil). Grapefruit seed extract is a natural preservative and is effective against both gram positive and gram negative bacteria. The polyoxyl 40 castor oil was heated and stirred to a temperature of about 100° F. Then the grapefruit seed oil and a cannabidiol oil containing 80 wt % cannabidiol (CBD) were added slowly and mixed until a clear viscous solution was formed containing dissolved grapefruit seed extract and cannabidiol oil. The clear emulsion was then slowly added to warm water (120° F.-180° F.) until a crystal clear solution was formed. The weight percentage of each component in the formulation is presented in Table 2.

TABLE 2

Water Soluble Cannabidiol and
Grapefruit Seed Extract Composition
Water Soluble CBD and
Grapefruit Seed Extract Formula

| Ingredients | Wt % |
| --- | --- |
| Grapefruit seed Extract Oil | 0.5% |
| Cannabidiol Oil (80% CBD) | 2% |
| Water | 67.1% |
| Macrogolglycerol hydroxystearate 40 | 30% |
| Citric Acid | 0.2% |
| Total | 100% |

The water soluble formulation above contains 1.6 wt %, or 16 mg/ml cannabidiol. It is noted that in some embodiments, as shown in the table above, the formulation may also include pH modifiers, preservatives, etc., in minor amounts.

Example 4

The water soluble concentrate prepared in accordance with Table 2 can be added to water, beverages, or other emulsions to make a crystal clear, water soluble preservative or drink that is effective against both gram positive and gram negative bacteria.

Example 5

Water soluble compositions of essential flavor oils were formulated containing polyoxyl castor oil and an essential flavor oil. Most essential flavor oils contain from about 20% to about 45% alcohol. The polyoxyl castor oil (non-ionic surfactant) was heated and stirred to a temperature of about 100° F., and a pure orange essential oil (containing no alcohol) was slowly mixed with the polyoxyl castor oil until a clear viscous solution was formed containing dissolved essential orange oil. A cannabidiol hemp oil containing 80% cannabidiol was added to this emulsion. The orange essential oil/cannabidiol emulsion was then slowly added to warm water heated to between 120° F.-180° F. The warm water had been previously boiled to sterilize. A crystal clear solution was formed.

TABLE 3

Water Soluble Cannabidiol and
Orange Essential Oil Composition
Water Soluble CBD and
Orange Essential Oil Composition

| Ingredients | Wt % |
|---|---|
| Orange Oil Flavor | 1.25 |
| Cannabidiol Oil (80 wt % CBD) | 1 |
| Water | 72.45 |
| Polyoxyl castor oil | 25 |
| Sodium Benzoate | 0.06 |
| Potassium Sorbate | 0.04 |
| Citric Acid | 0.2 |
| Total | 100 |

The water soluble formulation above contains 0.8 wt %, or 8 mg/ml cannabidiol. It is noted that in some embodiments, as shown in the table above, the formulation may also include pH modifiers, preservatives, etc., in minor amounts.

Example 6

The water soluble concentrate prepared in accordance with Table 3 can be added to water, beverages, or other emulsions to make a crystal clear, water soluble drink with acceptable flavor without the need of an alcohol containing essential oil extract.

Example 7

A pharmacokinetic, bioavailability (blood absorption) study was conducted with the water soluble cannabidiol formulation from Example 1 above. Male Sprague-Dawley rats were administered 50 mg doses by oral gavage. Blood plasma samples were collected at various intervals from 0-24 hours, post dose, and the plasma concentration of cannabidiol was determined by liquid chromatography/tandem mass spectrometry (LC-MS/MS). The animal data collected is shown in Table 4A. FIG. 1 displays the blood plasma level for each rat and the mean blood plasma level of the three rats over a 24 hour period.

TABLE 4A

Animal Data
Oral (50 mg/rat, WS CBD)

| | Rat #, Mean, or SD | | | | |
|---|---|---|---|---|---|
| | 1 | 2 | 3 | Mean | SD |
| 0 hour (pre-dose) | 8.73 | 42.2 | 17.8 | 22.9 | 17.3 |
| 0.25 hour | 103 | 56.8 | 65.3 | 75.0 | 24.6 |
| 0.5 hour | 342 | 270 | 333 | 315 | 39.2 |
| 1.0 hour | 681 | 696 | 673 | 683 | 11.7 |
| 2.0 hours | 1470 | 742 | 1050 | 1087 | 365 |
| 4.0 hours | 1870 | 2110 | 1730 | 1903 | 192 |
| 8.0 hours | 1470 | 1280 | 1520 | 1423 | 127 |
| 24 hours | 451 | 509 | 463 | 474 | 30.6 |
| Animal Weight (kg) | 0.293 | 0.294 | 0.306 | 0.298 | 0.007 |
| Dose (mg/kg) | 171 | 170 | 163 | 168 | 4.03 |
| $C_{max}$ (ng/mL) | 1870 | 2110 | 1730 | 1903 | 192 |
| $t_{max}$ (hr) | 4.0 | 4.0 | 4.0 | 4.0 | 0.0 |
| $t_{1/2}$ (hr) | 9.64 | 10.3 | 10.1 | 10.0 | 0.347 |

TABLE 4A-continued

Animal Data
Oral (50 mg/rat, WS CBD)

| | Rat #, Mean, or SD | | | | |
|---|---|---|---|---|---|
| | 1 | 2 | 3 | Mean | SD |
| $MRT_{last}$ (hr) | 8.65 | 9.15 | 8.93 | 8.91 | 0.250 |
| $AUC_{last}$ (hr · ng/mL) | 26789 | 24958 | 26317 | 26021 | 951 |
| $AUC_{\infty}$ (hr · ng/mL) | 33062 | 32526 | 33096 | 32895 | 320 |
| Dose-normalized Value $AUC_{last}$ (hr · kg · ng/mL/mg) | 157 | 147 | 161 | 155 | 7.37 |
| Dose-normalized Vlaue $AUC_{\infty}$ (hr · kg · ng/mL/mg) | 193 | 191 | 203 | 196 | 6.26 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_{\infty}$: area under the curve, extrapolated to infinity;
ND: not determined; and
Dose-normalized by dividing the parameter by the nominal dose in mg/kg.

In Table 4A, pharmacokinetic parameters were determined with Phoenix WinNonlin (v6.3) software using a non-compartmental model. The maximum plasma concentration ($c_{max}$) and the time to reach maximum plasma drug concentration ($t_{max}$) after oral dosing were observed from the data. The area under the time-concentration curve (AUC) was calculated using the linear trapezoidal rule with calculation to the last quantifiable data point, and with extrapolation to infinity if applicable. Plasma half-life ($t_{1/2}$) was calculated from 0.693/slope of the terminal elimination phase. Mean residence time, MRT, was calculated by dividing the area under the moment curve (AUMC) by the AUC. Any samples below the limit of quantization (0.5 ng/mL) were treated as zero for pharmacokinetic data analysis.

Example 8

Figure 2:
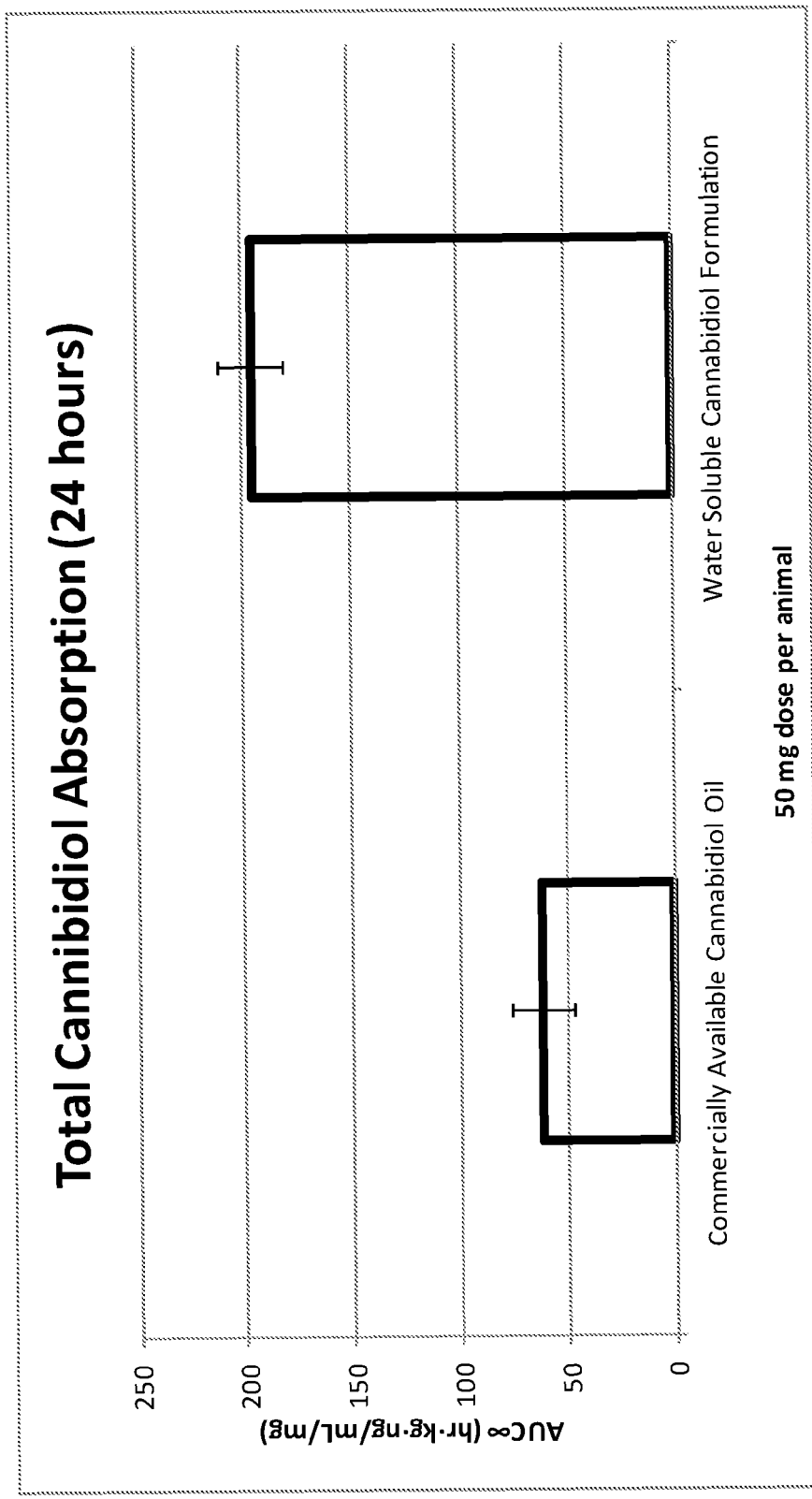
FIG. 2 shows a comparison of the total absorption for a sample formulation of the water soluble cannabidiol oil as disclosed herein to the absorption of a commercially available cannabidiol oil.

The concentration of drug in blood plasma against time was computed using the linear trapezoidal rule to determine the area under the curve (AUC). The mean AUC value to infinity from above was compared to previously determined cannabidiol oil absorption values for a typically available commercial formulation that was not dissolved in water and surfactant as disclosed herein. The results indicate, as shown in Table 4B, that the formulation from Example 1 exhibited approximately three times the absorption rate of the commercially available oil formulation. A graph of the absorption comparison is shown in FIG. 2.

TABLE 4B

Absorption Comparison Data

| Treatment | Total Absorption Level $AUC_{\infty}$ (hr · kg · ng/mL/mg) |
|---|---|
| Cannabidiol Oil | 62 |
| WS Cannabidiol Formulation | 196 |

While the above examples are illustrative of the principles and concepts discussed herein, it will be apparent to those of ordinary skill in the art that numerous modifications in form, usage and details of implementation can be made without the exercise of inventive faculty, and without departing from those principles and concepts. Accordingly, it is not intended that the principles and concepts be limited, except as by the claims set forth below.

What is claimed is:

1. A water-soluble phytocannabinoid emulsion formulation, comprising:
   a phytocannabinoid oil; and
   a non-ionic surfactant, wherein the non-ionic surfactant comprises a polyoxyl castor oil,
   wherein the weight ratio of phytocannabinoid content to non-ionic surfactant is from 1:10,000 to 1:5.

2. The formulation of claim 1, further comprising water.

3. The formulation of claim 2, wherein said formulation is a non-alcoholic formulation.

4. The formulation of claim 2, wherein said formulation is a non-aprotic solvated formulation.

5. The formulation of claim 2, wherein said phytocannabinoid is present at a concentration of at least 0.01 mg/ml.

6. The formulation of claim 2, wherein said phytocannabinoid is present at a concentration of at least 1 mg/ml.

7. The formulation of claim 2, wherein said phytocannabinoid is present at a concentration of at least 0.01% by weight.

8. The formulation of claim 2, wherein the formulation comprises from about 1 mg to about 50 mg of the phytocannabinoid.

9. The formulation of claim 1, wherein the phytocannabinoid oil comprises hemp oil.

10. The formulation of claim 1, wherein the formulation is devoid of water and a phytocannabinoid compound is present at a concentration of at least 0.1 mg/ml.

11. The formulation of claim 1, wherein the formulation is devoid of water and a phytocannabinoid compound is present at a concentration of at least 1 mg/ml.

12. The formulation of claim 1, wherein the formulation is devoid of water and a phytocannabinoid compound is present at a concentration of at least 0.1% by weight.

13. The formulation of claim 1, wherein the formulation is devoid of water and comprises from about 1 mg to about 75 mg of a phytocannabinoid compound.

14. The formulation of claim 1, wherein the formulation comprises at least about 10 mg of a phytocannabinoid compound.

15. The formulation of claim 1, wherein said non-ionic surfactant further comprises a member selected from the group consisting of a non-ionic water soluble mono-, di-, or tri-glyceride; non-ionic water soluble mono- or di-fatty acid ester of polyethyelene glycol; non-ionic water soluble sorbitan fatty acid ester; polyglycolyzed glyceride; non-ionic water soluble triblock copolymers; and a derivative thereof.

16. The formulation of claim 1, wherein said non-ionic surfactant further comprises a non-ionic water soluble mono-, di-, or tri-glyceride.

17. The formulation of claim 1, wherein the non-ionic surfactant consists of polyoxyl castor oil.

18. The formulation of claim 17, wherein the water-soluble phytocannabinoid emulsion is clear with a purple color.

19. The formulation of claim 1, wherein the water-soluble phytocannabinoid emulsion is clear with a purple color.

20. The formulation of claim 1, wherein the phytocannabinoid formulation comprises cannabidiol.

21. The formulation of claim 1, wherein the formulation is an oral formulation in a form of a fluid within soft gel capsule.

22. The formulation of claim 1, wherein the formulation is an oral formulation in a form of a tablet.

23. The formulation of claim 2, wherein the formulation is an oral formulation in a form of a beverage.

24. The formulation of claim 1, wherein the formulation is a topical formulation.

25. The formulation of claim 2, wherein the formulation is a topical formulation.

26. The formulation of claim 1, further comprising a pharmaceutically acceptable excipient.

27. The formulation of claim 2, wherein the water is present at greater than about 50 wt % and the formulation, and the formulation is clear with no visible particles or micelles to the naked eye.

28. A method of dissolving the water-soluble phytocannabinoid emulsion formulation of claim 1 in water, said method comprising the steps of:
   obtaining the phytocannabinoid oil, said phytocannabinoid oil containing a phytocannabinoid compound selected from the group consisting of cannabidiol (CBD), cannabinol (CBN), cannabichromene (CBC), cannabichromenic acid (CBCA), cannabidiolic acid (CBDA), cannabidivarin (CBDV), cannabigerol (CBG), cannabigerolic acid (CBGA), cannabigerivarin (CBGV), esters thereof, salts thereof, metabolites thereof, prodrugs thereof, and mixtures thereof;
   combining the phytocannabinoid oil with the non-ionic surfactant that has been heated to at least 90° F. to form a surfactant-phytocannabinoid mixture; and
   combining the surfactant-phytocannabinoid mixture with water that has been warmed to from 90° F. to 200° F., thereby dissolving surfactant-phytocannabinoid mixture in the water.

29. The method of claim 28, wherein the non-ionic surfactant is heated to from 90° F. to 200° F. to form the surfactant-phytocannabinoid mixture.

30. A method of delivering a phytocannabinoid compound to a subject, comprising administering the formulation of claim 1 to the subject, wherein the formulation adapts the phytocannabinoid compound in such a manner to allow for enhanced and improved bioavailability of said phytocannabinoid to the subject when compared to an undissolved or undispersed oil form of the phytocannabinoid.

31. A method of delivering a phytocannabinoid compound to a subject, comprising administering the formulation of claim 2 to the subject, wherein the formulation adapts the phytocannabinoid compound in such a manner to allow for enhanced and improved bioavailability of said phytocannabinoid to the subject when compared to an undissolved or undispersed oil form of the phytocannabinoid.

32. A water-soluble phytocannabinoid emulsion formulation, comprising:
   a phytocannabinoid oil containing a phytocannabinoid compound selected from the group consisting of cannabidiol (CBD), cannabinol (CBN), cannabichromene (CBC), cannabichromenic acid (CBCA), cannabidiolic acid (CBDA), cannabidivarin (CBDV), cannabigerol (CBG), cannabigerolic acid (CBGA), cannabigerivarin (CBGV), esters thereof, metabolites thereof, and mixtures thereof; and
   a non-ionic surfactant, wherein the non-ionic surfactant comprises a polyoxyl castor oil,
   wherein the phytocannabinoid content and the non-ionic surfactant are present in the formulation at a weight ratio from about 1:1,000 to about 1:5.

33. The formulation of claim 32, further comprising water.

34. The formulation of claim 32, wherein the formulation is devoid of water.

35. The formulation of claim 32, wherein the non-ionic surfactant further comprises a member selected from the group consisting of a non-ionic water soluble mono-, di-, or tri-glyceride; non-ionic water soluble mono- or di-fatty acid ester of polyethyelene glycol; non-ionic water soluble sorbitan fatty acid ester; polyglycolyzed glyceride; non-ionic water soluble triblock copolymers; and a derivative thereof.

36. The formulation of claim 32, wherein the non-ionic surfactant consists of polyoxyl castor oil.

37. A method for enhancing the bioavailability of a phytocannabinoid compound in a subject, comprising administering to the subject the water-soluble phytocannabinoid emulsion formulation of claim 1 comprising a phytocannabinoid oil extract and the non-ionic surfactant.

38. The method of claim 37, wherein the formulation is in a form of a liquid consumable.

39. The method of claim 38, wherein the liquid consumable further comprises at least 50 wt % water and the phytocannabinoid oil extract is solubilized or finely dispersed in the water to form a clear solution.

40. The method of claim 37, wherein the formulation is contained within a soft gelatin capsule.

41. The method of claim 37, wherein the formulation is in a form of a solid consumable.

42. The method of claim 37, wherein the formulation is in a form of a topical or injectable formulation.

43. The method of claim 37, wherein the phytocannabinoid oil extract is selected from the group consisting of cannabidiol (CBD), cannabinol (CBN), cannabichromene (CBC), cannabichromenic acid (CBCA), cannabidiolic acid (CBDA), cannabidivarin (CBDV), cannabigerol (CBG), cannabigerolic acid (CBGA), cannabigerivarin (CBGV), esters thereof, salts thereof, metabolites thereof, prodrugs thereof, and mixtures thereof.

* * * * *